United States Patent [19]

Speier et al.

[11] Patent Number: 4,719,024

[45] Date of Patent: Jan. 12, 1988

[54] METHYLALKYLCYCLOSILOXANES

[75] Inventors: John L. Speier; James R. Malek, both of Midland, Mich.

[73] Assignee: Dow Corning Corporation, Midland, Mich.

[21] Appl. No.: 859,547

[22] Filed: May 5, 1986

[51] Int. Cl.[4] .......................................... C10M 105/76
[52] U.S. Cl. .................... 252/49.6; 252/78.3; 556/460
[58] Field of Search ............................ 252/49.6, 78.3; 556/460

[56] References Cited

U.S. PATENT DOCUMENTS

| | | | |
|---|---|---|---|
| 3,197,432 | 7/1965 | Lamoreaux | 556/460 |
| 3,671,433 | 6/1972 | Brenner | 252/49.6 |
| 3,989,733 | 11/1976 | Okamoto et al. | 556/460 |
| 4,329,482 | 5/1982 | Elsheikh | 556/460 |

*Primary Examiner*—Jacqueline V. Howard
*Attorney, Agent, or Firm*—Dennis H. Rainear

[57] ABSTRACT

The invention relates to methylalkylcyclosiloxanes wherein each silicon atom in the siloxane ring has a methyl attached and each siloxane ring has at least two different non-methyl alkyl groups. The methylalkylcyclosiloxanes display a wide range of viscosity and thermal stability.

16 Claims, No Drawings

METHYLALKYLCYCLOSILOXANES

BACKGROUND OF THE INVENTION

Hydraulic fluids used in supersonic aircraft, missiles, and space crafts and materials used as brake fluids must meet very demanding performance criteria. The extreme variation in temperatures encountered between the high temperature of space travel re-entry and the low temperature of space severely limit the number and type of fluid materials which can be employed. Such temperature changes usually produce dramatic viscosity changes in fluids used in the craft which subsequently require compensation by mechanical parts. Frequently, such compensation is impractical or impossible and a substitute fluid must be found.

One class of fluid materials previously investigated as lubricants and hydraulic fluids for missiles and space craft includes silahydrocarbons, $SiR^1R^2R^3R^4$, where R is an alkyl group of one to twenty carbon atoms. Various materials within this class were found to have desirable properties of thermal stability up to 700 degrees F.; stable viscosity at temperatures ranging from −65 degrees to 400 degrees F.; excellent oxidative stability; low freezing points; and excellent lubricity.

However, silahydrocarbons are difficult and expensive to prepare. An inexpensive chemical synthesis of economic hydraulic, lubricating, and brake fluids, with all or most of the properties of silahydrocarbons, is therefore needed.

Alkylmethylpolysiloxanes have been investigated for such applications. The benefits of silicones for uses as hydraulics, lubricants, and brake fluids were recognized early in the development of these unique materials. McGregor et al., U.S. Pat. No. 2,398,187, issued Apr. 9, 1946, disclosed the broad generic use of linear dialkyl siloxane polymer and copolymer fluids for such applications on the basis of their slight change in viscosity with temperature, low pour point and high flash point. In addition, McGregor et al. recognized other beneficial properties, including: low volatility, low hygroscopicity, little or no corrosive or decomposing effect upon metal and rubber hydraulic device components, and little or no gasification or solidification tendencies under the higher or lower temperature conditions encountered in the various types of hydraulic applications.

More recently, commercial attention has focused on polydimethylsiloxanes (PDMS) as viable alternatives to the glycol-based polyethers traditionally employed in many hydraulic systems. This is not surprising, since PDMS represents the most ubiquitous and inexpensive silicone of manufacture. PDMS will not absorb or dissolve a significant amount of water and is amenable to lubricity additives. However, PDMS fluids have a disadvantage of a relatively high (about −50 degrees C.) solidification temperature which precludes their use in certain applications. Such disadvantage was engineered out of these fluids by copolymerizing mono- and trifunctional units with the difunctional siloxanes to attain a non-regular structure, i.e., a branched siloxane, with a greatly reduced tendency to crystallize. An example of a non-linear siloxane was disclosed by Holbrook et al. in U.S. Pat. No. 4,137,189, issued Jan. 30, 1979. In this case, the object was to provide an hydraulic fluid which could be utilized in all fluid transmission systems of an automobile. This application demanded greater lubricity on metals than ordinarily required in brake fluid applications. Thus Holbrook et al. disclosed a composition consisting essentially of a branched siloxane fluid, a chlorendate diester and a lubricant additive selected from dithiocarbamates and phosphorodithioates of antimony and lead.

A variation on the teachings of Holbrook et al. was disclosed by Keil in U.S. Pat. No. 4,443,351, issued Apr. 17, 1984, wherein it was suggested that the less expensive, linear polydimethylsiloxanes, or copolymers of PDMS with alkylmethyl siloxanes, be blended with a chlorendate diester, a lubricant additive (as above) and a block copolymer of polydimethylsiloxane-polybutadiene.

Brenner, in U.S. Pat. No. 3,671,433, issued June 20, 1972, disclosed the enhancement of alkylmethyl polysiloxane fluid lubricity with the addition of small amounts of dodecenyl succinic acid. It was shown that when the alkyl groups contained from 6 to 18 carbon atoms superior lubrication properties resulted. Brenner, however, does not teach the use of cyclic alkylmethylsiloxanes as in the instant invention.

Many patents address the preparation and use of cyclic polysiloxanes. However, to the knowledge of the applicants, no one has taught the preparation of the mixed methylalkyl tri- and tetracyclosiloxanes of the instant invention wherein each silicon atom has bonded to it one methyl group and one alkyl group and wherein two or more different alkyl groups larger than methyl are also bonded to silicon atoms in the cyclosiloxane.

SUMMARY OF THE INVENTION

This invention relates to the hydrolysis of mixtures of methylalkyldihalosilanes or methylalkyldialkoxysilanes to make mixed cyclic methylalkylsiloxanes at thermodynamic equilibrium containing two or more different alkyl groups larger than methyl. The instant invention also relates to a composition, consisting essentially of a mixture of cyclic methylalkylsiloxanes having the general formula $((CH_3)_2SiO)_a(CH_3R'SiO)_b(CH_3R''SiO)_c(CH_3R'''SiO)_d(CH_3R''''SiO)_e$ wherein a+b+c+d+e equals 3 or 4, and wherein b, c, d, and e are each, independently, zero, one, two or three and wherein R', R'', R''', and R'''' are each alkyl radicals different from each other and having from two to twenty carbon atoms, and wherein at least two values of b, c, d, and e are each greater than zero, and wherein the value of a can be zero or 1 when a+b+c+d+e equals 3, and wherein the value of a can be zero, 1 or 2 when a+b+c+d+e equals 4. R', R'', R''' and R'''' are independently selected from the group of alkyl radicals consisting of ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl.

DETAILED DESCRIPTION OF THE INVENTION

Unlike linear siloxanes of the type $(CH_3)_3SiO(SiCH_3RO)_nSi(CH_3)_3$, which lose hexamethyldisiloxane, $((CH_3)_3Si)_2O$, at high temperatures or under high vacuum, mixed cyclic siloxanes of the formula $(CH_3SiRO)_x$, where x is 3 or 4, are predominantly fluids of great stability of viscosity. This viscosity stability exists because the mixed cyclic siloxanes may be mixtures at nearly thermodynamic equilibrium. By "mixed" in the instant invention is meant those mixed methylalkylcyclosiloxanes in which two or more different non-methyl alkyl radicals are present on the same cyclic siloxane. The mixtures are excellent materials for hydraulic fluids and lubricants stable over a wide temperature range.

The instant invention can be illustrated by the following reaction;

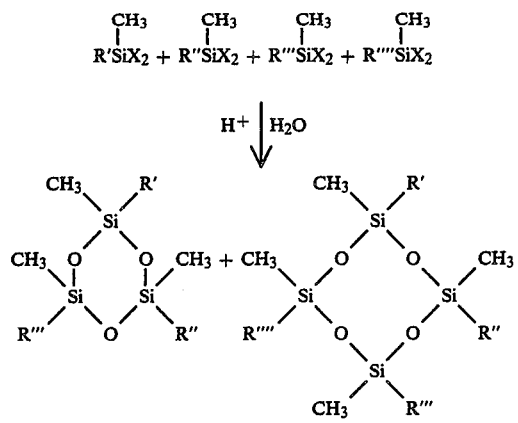

where X can be a halogen or an alkoxy group. In these reactions, R', R", R'" and R"" are preferably dissimilar. In addition to the cyclic trimeric siloxanes and tetrameric siloxanes indicated above there are produced the randomly mixed methylalkyl cyclosiloxanes wherein the alkyl radicals R', R", R'" and R"" may appear in any ratio on each cyclic ring. In addition to the cyclic trimeric and tetrameric siloxanes indicated above, there are also produced small amounts of the higher cyclic siloxane homologues, i.e. pentameric, hexameric, etc. The alkyl radicals used in the instant invention exhibit a statistically random distribution over the mixture of monomer units in cis and trans configurations of cyclosiloxanes. Thus the methylcyclosiloxanes of the instant invention can be depicted by the following formula

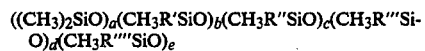

where R', R", R'" and R"" are each alkyl radicals different from each other and having from two to twenty carbon atoms, and wherein at least two of the values of b, c, d and e are each greater than zero, and wherein b, c, d and e are each, independently, zero, one, two or three, and wherein $a+b+c+d+e$ equals 3 or 4, and wherein the value of a can be zero or 1 when $a+b+c+d+e$ equals 3, and wherein the value of a can be 0, 1 or 2 when $a+b+c+d+e$ equals 4.

The instant invention also relates to a mixture comprising methylalkylcyclotrisiloxanes and methylalkycyclotetrasiloxanes wherein each methylalkylcyclosiloxane has the general formula

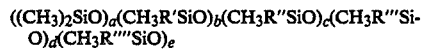

wherein R', R", R'" and R"" are each alkyl radicals different from each other and having from two to twenty carbon atoms, and wherein b, c, d, and e are each, independently, zero, one, two or three, and wherein at least two of the values of b, c, d, and e are each greater than zero, and wherein $a+b+c+d+e$ equals three or four, and wherein the value of a can be zero, or one when $a+b+c+d+e$ equals three, and wherein the value of a can be zero, one or two when $a+b+c+d+e$ equals four.

By way of example, the instant invention can be illustrated statistically by the following; Using a 1:1:1 equimolar mixture of monomeric methylalkyldihalo- or dialkoxy silanes, wherein the alkyl groups, R', R", and R'" differ, the statistical distribution of the mixed cyclic trimer methylalkylsiloxanes produced by the hydrolysis is

| | |
|---|---|
| R'R'R' | $3.703703 \times 10^{-2}$ |
| R"R"R" | $3.703703 \times 10^{-2}$ |
| R'"R'"R'" | $3.703703 \times 10^{-2}$ |
| R'R'R" | 0.111111 |
| R'R'"R' | 0.111111 |
| R"R'R" | 0.111111 |
| R"R'"R" | 0.111111 |
| R'"R'R'" | 0.111111 |
| R'"R"R'" | 0.111111 |
| R'R"R'" | 0.222222 |
| TOTAL | 0.999999 |

Thus the most prevalent combination of alkyl groups on any one cyclotrisiloxane is the combination R'R"R'". However, all combinations are present in the reaction mixture. The above statistical representation does not include the additional cis/trans isomer distinction which exists in the mixed compositions of the present invention. Similar calculations of the statistically random distribution for a cyclic tetramer show the mixed species R'R"R'"R"" to be the most common.

The mixtures of the present invention may be prepared by methods which are well known in the art. For example, they may be synthesized by cohydrolysis and cyclization of the appropriate diorganodialkoxysilanes or diorganodihalosilanes. The prior art utilization of cyclic siloxanes is predominantly directed toward the production of intermediates which are subsequently ring opened to produce desired end products in the polymerization of linear polysiloxanes. The instant invention is related to the use of the mixed methylalkylcyclosiloxanes themselves rather than as a precursor to linear polymers.

The instant invention also relates to the formation of hydraulic fluids and lubricants by the hydrolysis of mixtures of the methylalkyldihalosilanes or methylalkyldialkoxysilanes to produce mixtures of cyclic methylalkylsiloxanes where each cyclic ring preferably contains three or four silicon atoms and two or more differing non-methyl alkyl groups. The hydrolysis of a mixture of methylalkyldihalo- or methylalkyldialkoxysilane starting materials wherein two or more different non-methyl alkyl groups are present produces cyclosiloxane products of extremely asymmetric structures which consequently cannot easily arrange into a crystalline structure. The selection and combinations of R groups of the starting materials permit the formation of hydrolysis products of the instant invention of extreme range of fluid properties, and which are very non-volatile and low temperature freezing. Such R groups include ethyl, isopropyl, linear, branched or cyclic alkyl groups up to and including eicosyl.

The mixed fluids of the instant invention have very low freezing points and should display marked reduction in vapor pressure over that of ordinary alkylsiloxanes. Table 1 illustrates the observed freezing points of several mixtures according to the instant invention.

TABLE 1

Freezing Points of Mixed Methylalkylcyclosiloxanes
$((CH_3)_2SiO)_a(CH_3R'SiO)_b(CH_3R''SiO)_c(CH_3R'''SiO)_d(CH_3R''''SiO)_e$

| Sample | R':R'':R''':R'''' | Molar ratio | Freezing Point, °C |
|---|---|---|---|
| 1 | $C_6H_{13}:C_8H_{17}:C_{10}H_{21}$ | 1:1:1 | −45 |
| 2 | $C_6H_{13}:C_8H_{17}$ | 1:1 | −63 |
| 3 | $C_6H_{13}:C_8H_{17}$ | 2:1 | −69 |
| 4 | $C_2H_5:C_6H_{13}:C_8H_{17}$ | 1:5:4 | −72 |
| 5 | $C_6H_{13}:C_8H_{17}$ | 5:4* | −68 |
| 6 | $C_6H_{13}:C_8H_{17}:C_{10}H_{21}$ | 1:1:1* | −49 |
| 7 | $C_6H_{13}:iso-C_8H_{17}$ | 1:1 | −78 |
| 8 | $cyclo-C_6H_{11}:C_8H_{17}$ | 1:1 | −67 |
| 9 | $C_2H_5:C_6H_{13}:C_{20}H_{41}$ | 1:8:1 | −40 |
| 10 | $C_6H_{13}:C_8H_{17}:C_{20}H_{41}$ | 1:1:1 | +35 |

*$(CH_3)_2SiO$, was incorporated into the cyclosiloxanes, i.e., the value of a was equal to one.

The freezing points depicted in Table 1 are very much lower than the freezing points known in the literature for non-mixed cyclic siloxanes, as shown in Table 2.

TABLE 2

| | Cyclic siloxane | Freezing Point, C. |
|---|---|---|
| 1 | $((CH_3)_2SiO)_3$ | +65 |
| 2 | $((CH_3)_2SiO)_2(CH_3C_2H_5SiO)$ | −8 |
| 3 | $((C_2H_5)_2SiO)_3$ | +14 |
| 4 | $((CH_3)(C_3H_7)SiO)_3$ | −13 |
| 5 | $((CH_3)_2SiO)_4$ | +18 |
| 6 | $((C_2H_5)_2SiO)_4$ | −50 |
| 7 | $((CH_3)(C_2H_5)SiO)_4$ | −40 |
| 8 | $((CH_3)(C_{12}H_{25})SiO)_3$ | +31 |

(Values for the freezing points in Table 2 were obtained from Bazant, et al., Organosilicon Compounds, Volumes 2 and 3, Publishing House of the Czechoslovak Academy of Sciences, Prague 1965.)

EXAMPLE 1

This example illustrates the manufacture of mixed cyclic methylalkylsiloxanes. $CH_3Cl_2Si-n-C_6H_{13}$ (40 grams, 0.2 mole); $CH_3Cl_2Si-n-C_8H_{17}$ (45 grams, 0.2 mole) and $CH_3Cl_2Si-n-C_{10}H_{21}$ (51 grams, 0.2 mole) were mixed and dissolved in ether (300 milliliters). The solution was added with stirring to 140 grams of crushed ice (7.8 moles of water). When the slurry warmed to room temperature, the ether solution of the hydrolysate was separated from the aqueous layer of hydrochloric acid. The ether was evaporated under vacuum from the solution of hydrolysate, which was then diluted with hexane and washed repeatedly with a saturated solution of $NaHCO_3$ in water to remove all traces of acid and then with distilled water to remove any basic materials. The washed hexane solution was stripped free of hexane and water and filtered through a fine fritted glass filter. The freezing point of this mixed methylalkylcyclosiloxane was approximately −45 degrees Centigrade. Infra red analysis showed a small amount of silanol −OH and mostly cyclic trimer with some cyclic tetramer methylsiloxane structures. When analyzed at 37.8 degrees Centigrade for thermal stability after 6 hours at 371 degrees Centigrade under nitrogen, the mixture showed only 0.5% viscosity change by ASTM D446, and 0.00 change in acid number by ASTM D664.

EXAMPLE 2

Using the same procedure as that described in Example 1, a mixed methylalkylcyclosiloxane with the following alkyl radicals was prepared; $C_6H_{13}$ and $C_8H_{17}$ in a 1:1 molar ratio. The freezing point was approximately −63 degrees Centigrade.

EXAMPLE 3

Using the same procedure as that described in Example 1, a mixed methylalkylcyclosiloxane with the following alkyl radicals was prepared; $C_6H_{13}$ and $C_8H_{17}$ in a 2:1 molar ratio. The freezing point was approximately −69 degrees Centigrade.

EXAMPLE 4

Using the same procedure as that described in Example 1, a mixed methylalkylcyclosiloxane with the following alkyl radicals was prepared; $C_2H_5$, $C_6H_{13}$ and $C_8H_{17}$ in a 1:5:4 molar ratio. The freezing point was approximately −72 degrees Centigrade.

EXAMPLE 5

Using the same procedure as that described in Example 1, a mixed methylalkylcyclosiloxane with the following alkyl radicals was prepared; $CH_3$, $C_6H_{13}$ and $C_8H_{17}$ in a 1:5:4 molar ratio. The freezing point was approximately −68 degrees Centigrade.

EXAMPLE 6

Using the same procedure as that described in Example 1, a mixed methylalkylcyclosiloxane with the following alkyl radicals was prepared; $CH_3$, $C_6H_{13}$, $C_8H_{17}$, and $C_{10}H_{21}$ in a 1:3:3:3 molar ratio. The freezing point was approximately −49 degrees Centigrade.

EXAMPLE 7

Using the same procedure as that described in Example 1, a mixed methylalkylcyclosiloxane with the following alkyl radicals was prepared; $C_6H_{13}$ and $C_8H_{19}$ in a 1:1 molar ratio. The freezing point was approximately −78 degrees Centigrade.

EXAMPLE 8

Using the same procedure as that described in Example 1, a mixed methylalkylcyclosiloxane with the following alkyl radicals was prepared; $C_6H_{11}$ and $C_8H_{17}$ in a 1:1 molar ratio. The freezing point was approximately −67 degrees Centigrade. The $C_6H_{11}$ radical in this example was cyclohexyl.

EXAMPLE 9

Using the same procedure as that described in Example 1, a mixed methylalkylcyclosiloxane with the following alkyl radicals was prepared; $C_2H_5$, $C_6H_{13}$, and $C_{20}H_{41}$ in a 1:8:1 molar ratio. The freezing point was approximately −40 degrees Centigrade.

EXAMPLE 10

Using the same procedure as that described in Example 1, a mixed methylalkylcyclosiloxane with the following alkyl radicals was prepared; $C_6H_{13}$, $C_8H_{17}$, and $C_{20}H_{41}$ in a 1:1:1 molar ratio. The freezing point was approximately +35 degrees Centigrade.

That which is claimed is:

1. A methylalkylcyclosiloxane having the general formula $((CH_3)_2SiO)_a(CH_3R'SiO)_b(CH_3R''SiO)_c(CH_3R'''SiO)_d(CH_3R''''SiO)_e$ and wherein R', R'', R''', and R'''' are each alkyl radicals different from each other and having from two to twenty carbon atoms, and wherein b, c, d, and e are each, independently zero, one, two or three, and wherein at least two of the values of b, c, d, and e are each greater than zero, and wherein a+b+c+d+e equals 3 or 4, and wherein the value of a can be zero, or one when a+b+c+d+e equals 3, and wherein the value of a can be zero, one or two when $a+b+c+d+e$ equals 4.

2. A mixture comprising one or more methylalkylcyclotrisiloxanes and one or more methylalkylcyclotetrasiloxanes wherein each methylalkylcyclosiloxane has the general formula $((CH_3)_2SiO)_a(CH_3R'SiO)_b(CH_3R''SiO)_c(CH_3R'''SiO)_d(CH_3R''''SiO)_e$ wherein R', R'', R''' and R'''' are each alkyl radicals different from each other and having from two to twenty carbon atoms, and wherein b, c, d, and e are each independently zero, one, two, or three, and wherein at least two of the values of b, c, d, and e are each greater than zero, and wherein $a+b+c+d+e$ equals three or four, and wherein the value of a can be zero, or one when $a+b+c+d+e$ equals three, and wherein the value of a can be zero, one or two when $a+b+c+d+e$ equals four.

3. A hydraulic fluid comprising the composition of claim 2.

4. A brake fluid comprising the composition of claim 2.

5. A lubricating fluid comprising the composition of claim 2.

6. A methylalkylcyclosiloxane as claimed in claim 1 wherein R' is hexyl, R'' is octyl, R''' is decyl, a is zero, b is one, c is one, d is one and e is zero.

7. A methylalkylcyclosiloxane as claimed in claim 1 wherein R' is hexyl, R'' is octyl, a is zero, b is two, c is two, d is zero, and e is zero.

8. A methylalkylcyclosiloxane as claimed in claim 1 wherein R' is hexyl, R'' octyl, a is zero, b is two, c is one, d is zero, and e is zero.

9. A methylalkylcyclosiloxane as claimed in claim 1 wherein R' is ethyl, R'' is hexyl, R''' is octyl, a is zero, b is one, c is two, d is one, and e is zero.

10. A methylalkylcyclosiloxane as claimed in claim 1 wherein R' is hexyl, R'' is octyl, a is one, b is one, c is one, d is zero, and e is zero.

11. A methylalkylcyclosiloxane as claimed in claim 1 wherein R' is hexyl, R'' is octyl, R''' is decyl, a is one, b is one, c is one, d is one, and e is zero.

12. A methylalkylcyclosiloxane as claimed in claim 1 wherein R' is hexyl, R'' is octyl, a is two, b is one, c is one, d is zero and e is zero.

13. A methylalkylcyclosiloxane as claimed in claim 1 wherein R' is hexyl, R'' is octyl, R''' is eicosyl, a is zero, b is one, c is one, d is one, and e is zero.

14. A methylalkylcyclosiloxane as claimed in claim 1 wherein R' is ethyl, R'' is hexyl, R''' is eicosyl, a is zero, b is one, c is two, d is one and e is zero.

15. A mixture as claimed in claim 2, wherein in the methylalkylcyclotrisiloxane, R' is hexyl, R'' is octyl, R''' is decyl, a is zero, b is one, c is one, d is one, e is zero, and in the methylalkylcyclotetrasiloxane, R' is hexyl, R'' is octyl, R''' is decyl, a is zero, b is two, c is one, d is one, and e is zero.

16. A mixture as claimed in claim 2, wherein in one of the methylalkylcyclotrisiloxanes, R' is ethyl, R'' is hexyl, a is one, b is one, c is one, d is zero and e is zero, and wherein in another of the methylalkylcyclotrisiloxanes in the mixture, R' is ethyl, R'' is hexyl, R''' is eicosyl, a is zero, b is one, c is one, d is one, and e is zero, and wherein in one of the methylalkylcyclotetrasiloxanes in the mixture, R' is ethyl, R'' is hexyl, R''' is eicosyl, a is one, b is one, c is one, d is one and e is zero.

* * * * *